United States Patent [19]

Krespan

[11] 4,160,780

[45] Jul. 10, 1979

[54] 2-KETOPENTAFLUOROPROPANESUL-FONIC ACID AND RELATED ACIDS

[75] Inventor: Carl G. Krespan, Wilmington, Del.

[73] Assignee: E. I. Du Pont de Nemours and Company, Wilmington, Del.

[21] Appl. No.: 602,756

[22] Filed: Aug. 7, 1975

[51] Int. Cl.$^2$ ............................................. C07C 143/08
[52] U.S. Cl. ................................................. 260/513 F
[58] Field of Search ........................ 260/513 F, 456 F

[56] References Cited

PUBLICATIONS

Bekker et al., Chem. Abstract, 81, 169052(b) (1974).

*Primary Examiner*—Nicky Chan

[57] ABSTRACT

2-Ketopentafluoropropanesulfonic acid is obtained as a product of the reaction of sulfur trioxide and ethyl pentafluoroisopropenyl ether or by transesterification from corresponding esters. Similar sulfonic acids may be obtained by the latter process. The new compounds are useful as monomers for producing polymers, particularly moldable, dyeable, fluoropolymers, and as cationic initiators, e.g., for tetrahydrofuran polymerization.

2 Claims, No Drawings

2-KETOPENTAFLUOROPROPANESULFONIC ACID AND RELATED ACIDS

BACKGROUND OF THE INVENTION

1. Field of the Invention

This invention pertains to 2-ketopentafluoropropanesulfonic acid and related sulfonic acids, their preparation, and polymers made from the same.

2. Art

2-Ketopentafluoropropanesulfonic acid is shown by Bekker et al., 1.L (Inst. Elementoorg. Soedin., Moscow, USSR). Dokl. Acad Nauk SSSR 1974, 217 (6), 1320-3 [(Chem)] (Russ); Chem Abstr 81, 169,052(b) (1974). They report obtaining the compound by heating $CF_2=C(CF_3)$ $OSO_3H$.

SUMMARY OF THE INVENTION

The present invention provides ketoperfluorosulfonic acids of the formula $$R_f CF_2 \underset{\underset{R_f^2}{|}}{C} FSO_2OH,$$

where R and $R^2$, alike or different are fluorine or perfluoroaklyl of up to 4 carbons.

The invention also provides a process for preparing the sulfonic acids by transesterifying the corresponding methyl or ethyl esters with a strong acid. The esters are made according to the teachings of coassigned Ser. No. 602,757, filed Aug. 7, 1975.

The acids are useful as cationic initiators for tetrahydrofuran polymerization. They are also useful comonomers to make dyeable polymers with tetrafluoroethylene and vinylidene fluoride.

PREFERRED EMBODIMENTS OF THE INVENTION

In the present invention, 2-ketopentafluoropropanesulfonic acid (II) is prepared along with ethyl 2-ketopentafluoropropanesulfonate (III) by reacting sulfur trioxide with ethyl pentafluoroisopropenyl ether (I) according to the equation:

$$\underset{I}{CF_3\underset{\underset{OCH_2CH_3}{|}}{C}=CF_2} + SO_3 \longrightarrow \underset{III}{CF_3CCF_2SO_2OCH_2CH_3} +$$

$$\underset{II}{CF_3\overset{O}{\overset{\|}{C}}CF_2SO_2OH} \quad (1)$$

The reaction is generally carried out in liquid phase, at a temperature of about −40 to about +100° C., 0-50° being preferred. The reaction time can be short, in many cases the reaction being substantially completed within a few minutes at about 50°-100° C., but can be as long as a day, e.g., at about −40° C. to 0° C. Atmopsheric pressure is generally preferred, but pressures up to 3000 psi can be employed.

A solvent is not necessary, but media of low reactivity towards $SO_3$ may be used, especially halogenated solvents such as tetrachloroethylene and 1,1,2-trichloro-1,2,2-trifluoroethane. An excess of either reactant may be used if desired, but a ratio of the acyclic fluorovinyl ether to $SO_3$ close to 1:1 is preferred. Isolation is generally effected by distillation under reduced pressure.

Although the acid II is obtained directly as a coproduct in the reaction above, greatly increased yields are available by transesterification with other acids which are stable toward the powerfully acidic II according to the equations ($R_f$ is a perfluorinated radical such as $CF_3$, $C_3F_7$, etc.):

$$CF_3\overset{O}{\overset{\|}{C}}CF_2SO_2OCH_2CH_3 + R_fCOOH \longrightarrow$$
$$\underset{III}{}$$

$$CF_3\overset{O}{\overset{\|}{C}}CF_2SO_2OH + R_fCO_2CH_2CH_3 \quad (2)$$
$$\underset{II}{}$$

$$CF_3\overset{O}{\overset{\|}{C}}CF_2SO_2OCH_2CH_3 + H_2SO_4 \longrightarrow$$

$$CF_3\overset{O}{\overset{\|}{C}}CF_2SO_2OH + HOSO_2OCH_2CH_3 \quad (3)$$

Suitable acids for use as transesterification partners with III are the illustrated perfluoroalkylcarboxylic acids, e.g., trifluoroacetaic acid and sulfuric acid. In general, any strong acid which is stable toward II and boils lower or significantly higher than the desired sulfonic acid may be used. To carry out the transesterification, either a crude reaction product mixture containing ester III or purified ester III is treated with the acidic transesterification partner and allowed to stand at about 25° C. for a day or heated briefly at about 80° C. Pure II is isolated by fractional distillation.

Other ketosulfonic acids can be made by the transesterification process of this invention. Thus, methyl 2-keto-1-trifluoromethyltetrafluoropropanesulfonate [Ex. 4 of Ser. No. 602,757, now abandoned] will give $$CF_3\overset{O}{\overset{\|}{C}}\underset{\underset{CF_3}{|}}{C}FSO_2OH,$$

2-keto-1-trifluoromethyltetrafluoropropanesulfonic acid, on transesterification with $H_2SO_4$ or trifluoroacetic acid. The compound $$CF_3CF_2\overset{O}{\overset{\|}{C}}CF_2SO_2OCH_3,$$

methyl 2-ketoheptafluorobutane-1-sulfonate, prepared by treatment of perfluorobutanone-2 with trimethyl phosphite, to give 2-methoxyheptafluorobutene-1 which is then reacted with sulfur trioxide, will give $$CF_3CF_2\overset{O}{\overset{\|}{C}}CF_2SO_2OH,$$

2-ketoheptafluorobutanesulfonic acid.

The present acids, especially 2-ketopentafluoropropanesulfonic acid, are useful as comonomers for providing sulfonic acid groups when incorporated into fluoropolymers. Such sulfonic acid groups serve (for example)

as dyesites in solid fluoropolymers which otherwise would not accept a dye. A general formula for the polymers may be written as

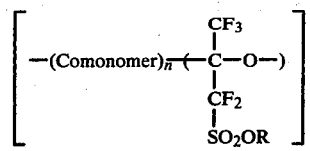

where n is 2–500 (n is the mole ratio of comonomer to sulfonic acid moiety) and R is H or $CF_2CH_3$. The comonomer may be vinylidene fluoride, tetrafluoroethylene or trifluoroethylene. As shown in the examples below, the product is a solid, heat-moldable, dyeable, heat-stable highly fluorinated copolymer, a molecular weight in excess of 50,000 being indicated. The following examples illustrate the practice and utility of the invention. Examples 1–4 show the preparation of 2-ketopentafluoropropanesulfonic acid and Examples 5–7 show the preparation of polymers from the acid. In the examples, temperatures are in degrees centigrade and percentages are by weight. F113 in Examples 5–7 is Freon®113, trichlorotrifluoethane.

EXAMPLE 1

Ethyl 2-Ketopentafluoropropane Sulfonate (III) and 2-Ketopentafluoropropanesulfonic Acid (II)

A. Dropwise addition of 12.8 g (0.16 mol) of $SO_3$ to 29.0 g (0.165 mol) of ethyl pentafluoroisopropenyl ether (D. W. Wiley and H. E. Simmons, J. Org. Chem. 29, 1876 (1974)) resulted in an exothermic reaction. Distillation of the black reaction mixture gave 6.3 g (22%) of crude recovered ether (identified by ir) and 20.2 g (49% conv. and 63% yield) of III, bp 47°–48° (12mm).

Spectral properties fit ring-opened ester III as the structure. Ir (neat) 3.34 and 3.41 (satd CH), 5.60 (C=O), 7.09 ($SO_2O$), 7.6–8.5 μ ($CF_2SO_2$): nmr $^1H$ 4.59 (q, $J_{HH}$7.2 Hz, 2,$OCH_2$), 1.51 ppm (t, $J_{HH}$7.2 Hz, 3, $CH_3$); $^{19}F$–75.0 (t,$J_{FF}$ 8.3 Hz, 3,$CF_3$), −107.4 ppm (q, $J_{FF}$8.3 Hz,2,$CF_2$).

B. Reaction of 176 g (1.0 mol) of ethyl pentafluoroisopropenyl ether and 88 g (1.1 mol) of $SO_3$ (Equation 1, above) was carried out similarly to A above, but at 0.5°. The colorless reaction mixture, which darkened on standing overnight, was distilled to give 28.6 g (16% of crude recovered vinyl ether, bp 46°–48°; 145.1 g (57% conv. and 68% yield) of III, bp 48°–52° (12mm); and a higher boiling cut composed mainly of II. Redistillation of the crude II gave 35.6 g (16% conv. and 19% yield) of II bp 81°–82° (6.2 mm).

For II, ir ($CCl_4$ between $CaF_2$ plates) broad 3.3 and 4.2 (SOH), 5.58 (C=O), 7.13$_{19}$ ($SO_2O$), 7.5–9 μ($CF_2SO_2$): nmr (neat) $^1H$ 10.2 ppm (s,$SO_2OH$); F-76.2 (t,$J_{FF}$7.5 Hz, 3,$CF_3$), −108 ppm (q,$J_{FF}$7.5 Hz,2,$CF_2$). Anal. Calcd for $C_3HF_5O_4S$: C, 15.80; H, 0.44; F, 41.65; S, 14.06. Found: C, 15.95; H, 0.55; F. 41.55: S, 13.89.

EXAMPLE 2

Preparation of 2-Ketofluoropropanesulfonic Acid From Ethyl Pentafluoroisopropenyl Ether, $SO_3$ and Trifluoroacetic Acid 17.6 g (1.0 mol) of ethyl pentafluoroisopropenyl ether was cooled between −5° and −10° C. and stirred while 50 g (1.0 mol) of $SO_3$ was added over a 1.5 hr period. The mixture was stirred at −10° for an additional 30 min. and then allowed to stand overnight. The yellow-orange product was warmed and gave an exothermic reaction which was controlled at temperatures below 40° by mild cooling. 125.4 g (1.1 mol) of trifluoroacetic acid was added, and the mixture was allowed to stand overnight and then fractionally distilled. After the removal of excess trifluoroacetic acid and $CF_3CO_2CH_2CH_3$, 99.2 g of crude 2-ketopentafluoropropanesulfonic acid was obtained representing a yield of 44%, b.p. 55–68 at 2.8 mm pressure.

EXAMPLE 3

Preparation of 2-Ketopentafluoropropanesulfonic Acid From Ethyl Pentafluoroisopropenyl Ether, $SO_3$ and $H_2SO_4$ 58.0 g (0.33 mol) of ethyl pentafluoroisopropenyl ether was cooled to about −15° while 25.6 g (0.32 mol) of $SO_3$ was being added. The mixture was stirred and allowed to warm. On heating to 47° for several minutes an exothermic reaction resulted, the temperature of the mixture rising to 65° before being controlled by cooling. The mixture was then distilled in a spinning band still. 19.9 of 2-ketopentafluoropropanesulfonic acid was obtained representing a yield of 27%, bp 47–45 at 0.9 mm pressure.

EXAMPLE 4

Transesterification of Ethyl 2-Ketopentafluoropropane Sulfonate to 2-Ketopentafluoropropanesulfonic Acid 25.6 g (0.10) mol of ethyl 2-ketopentafluoropropanesulfonate was stirred at 25° while 17.1 g (0.15 mol) of trifluoroacetic acid was added. The mixture was allowed to stand overnight, then heated on a spinning band still to reflux at 60°. Fractional distillation of the reaction mixture at pot temperatures below 100° and at a pressure of 2.6 mm resulted in the isolation of 18.4 g of 2-ketopentafluoropropanesulfonic acid, representing a yield of 81%, bp 73°.

EXAMPLE 5

Copolymerization of 2-Ketopentafluoropropane Sulfonic Acid with Vinylidene Fluoride ($VF_2$)

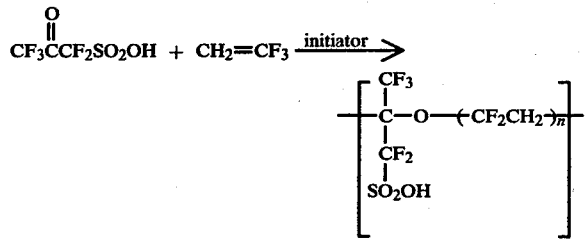

A 10-ml stainless steel tube was charged with 3.41 g (0.015 mol) of 2-ketopentafluoropropanesulfonic acid, 0.50 ml of 8% perfluoropropionyl peroxide in F113, 2 ml of F113, and 3.5 g (0.055 mol) of vinylidene fluoride, then heated at ca. 40° for 8 hr. Evaporation of volatiles under nitrogen followed by evacuation at 25° (<0.5 mm) overnight left 3.5 g of greasy polymer. Evacuation at 25° (< 0.5 mm) over the weekend left 3.1 g of residue, then at 70° (< 0.5 mm) for one day left 2.6 g of residual viscous copolymer. The polymer was stirred two times with 10 ml of water at 25° to remove the last of unreacted acid then dried at 25° (0.5 mm) to give 2.6 g of very viscous copolymer. Ir: 2.90 and 6.10 (HO), 3.29 and 3.34 (satd CH), 7-10 μ (CF,C—OC,SO₂) with unknown C=O at 5.66 μ. Nmr on a solution in DMSO-d₆ showed ¹⁹F resonances attributable to CF₃ and OCF₂ along with several other kinds of CF₂, while ¹H resonances for CF₂CH₃, OH, and two areas for CH₂ were observed.

Anal. Calcd for

C, 27.26; H, 2.56; S, 5.27. Found: 26.99; H, 2.63; S, 5.23.

EXAMPLE 6

Copolymerization of 2-Ketopentafluoropropanesulfonic Acid with Tetrafluoroethylene (TFE)

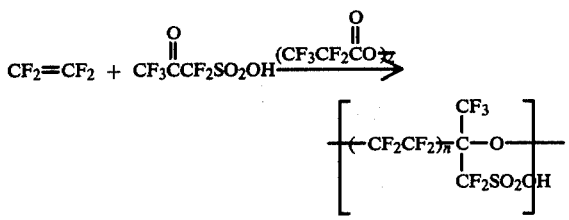

Copolymerizations of TFE with 2-ketopentafluoropropanesulfonic acid were carried out at varying pressures as follows:

A. A cold mixture of 20 ml of F113, 5.0 ml of 8% perfluoropropionyl peroxide in F113, and 4.6 (0.02 mol) of 2-ketopentafluoropropanesulfonic acid was charged into an 80 ml Hastelloy ®-lined tube, and 20 g (0.20 mol) of tetrafluoroethylene was added at −48°. As the tube warmed slowly, an exothermic polymerization starting near 8° carried the pressure to a maximum of 450 psi. The mixture was then heated at 30° for 2 hr. Product polymer was stirred with 50 ml of F113 and filtered, and the filter cake was thoroughly rinsed with F113. The polymer was then stirred with 150 ml of water, filtered and dried at 100° under vacuum. There was thus obtained 16.8 g of sulfonic acid. A gram of the solid polymer was stirred with conc. NH₄OH for 3 hr, filtered, and dried under vacuum at 25°. Sulfur analysis on a large sample gave S, 0.07%, corresponding to an equivalent weight of 46,000 and a ketosulfonic acid content of 0.5%, n in the general formula being 460.

B. A copolymerization similar to the above was carried out with 20 ml of F113, 2.0 ml of 8% perfluoropropionyl peroxide in F113, 22.8 g (0.10 mol) of 2-ketopentafluoropropanesulfonic acid, and 20 g (0.20 mol) of tetrafluoroethylene. The tube was pressured to 500 atm. with argon while still cold. As the reaction warmed to 6°, rapid polymerization caused a pressure increase and part of the gases was bled off. The product polymer was extracted with several portions of F113 and dried under vacuum to a colorless solid. A sample treated with conc. NH₄OH, washed, and dried under vacuum showed on analysis 0.85% S.

C. Reaction of 40 ml of F113, 1.0 ml of 8% perfluoropropionyl peroxide in F113, 22.8 g (0.10 mol) of 2-ketopentafluoropropionyl peroxide, and 20 g (0.20 mol) of tetrafluoroethylene was carried out in a 125-ml tube lined with stainless steel under 2500 atm. of nitrogen. The tube was warmed slowly to 30° and kept at 30° for 4 hr. Work-up of the polymer by extractions with F113 and with water gave 13.9 g (69%) of solid copolymer. A sample which was stirred with conc. NH₄OH, washed and dried was analyzed for N and S. For N, 0.12 and 0.15% correspond to an equivalent weight of 10,777 or 2.3% of ketosulfonic acid as the ammonium salt. For S, 0.18 and 0.10% correspond to an equivalent weight of 22,900 or 1.1% of comonomer, n in the general formula being 105.

D. Samples of copolymer prepared under different pressures as above and a control sample of essentially undyeable polytetrafluoroethylene prepared in the same system as the copolymers were exposed to the basic dye, Sevron ® Red GL. After exhaustive washing, the level of color in the polymer was taken as a rough measure of comonomer content. The fact that dyeing occurs is not only a demonstration that the comonomer containing an acid receptor site has been incorporated, since the control is not dyed under the same conditions, but also a useful property.

The general procedure was to stir 1.0 g of polymer with 50 ml of 1:1 H₂O/ethanol containing an excess of Du Pont Sevron ® Red GL. After 3 days, the polymer was recovered, stirred with portions of 1:1 H₂O/ethanol until dye was no longer being extracted (total of 4 washings), and dried under vacuum.

| Substrate | Result |
|---|---|
| polytetrafluoroethylene | essentially colorless |
| copolymer (100–400 psi) | pale orange-red |
| copolymer (500 atm. and neutralized with NH₄OH) | moderate depth orange-red |
| copolymer (2500 atm) | strongly orange-red |

EXAMPLE 7

Copolymerization of 2-Ketopentafluoropropanesulfonic Acid with Vinylidene Fluoride A. A sample of ester IV was prepared separately from 2-ketopentafluoropropanesulfonic acid and vinylidene fluoride.

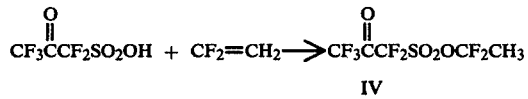

IV

A metal tube containing 23.8 g (0.10 mol) of sulfonic acid cooled below −40° and 13 g (0.20 mol) of vinylidene fluoride was added. The mixture was shaken as it warmed to 25° and was kept at 25° for 4 hr. Distillation of the liquid product gave 20.4 g (70%) of ester IV, bp 62°-63° (50 mm). Ir (CCl₄): 5.54 (C=O), 6.96 (SO₂O), and 7.5–94 (CF, SO). Nmr: ¹H 2.06 ppm (t,$J_{HF}$14.3 Hz, CH₃); ¹⁹F− 58.3 (q, $J_{HF}$14.3 Hz into t, $J_{FF}$7.1 Hz, 2F, OCF₂), −75.0 (t,$J_{FF}$ 8.0 Hz, 3F, CF), and −106.1 ppm (q, $J_{FF}$8.0 Hz, into overlapping triplets, $J_{FF}$7.1 Hz, 2F, CF₂SO₂).

Anal. Calcd for C₅H₃F₇O₄S: C, 20.56; H, 1.03; F, 45.52. Found: C, 20.73; H, 1.03; F, 45.72.

B. Monomer IV from A was copolymerized with vinylidene fluoride as follows:

A cold mixture of 20 ml of F113, 5 ml of 8% perfluoropropionyl proxide, and 10.9 g (0.037 mol) of IV was loaded into an 80-ml Hastelloy ®-lined tube. After 20 g (0.32 mol) of vinylidene fluoride was added at −40°, the mixture was shaken while it warmed to 25°. After 20 hr at 25°, volatiles were removed under reduced pressure to leave 25.8 g (83% based on a content of 64% vinylidene fluoride) of white solid copolymer. A sample was stirred with 250 ml of water for 4 hr, filtered and dried under vacuum. Ir (KBr): similar spectrum to that of poly(vinylidene fluoride), with broadened bands and additional absorptions also present; a 5.6 μ band suggests some C=O or C=CF$_2$ present.

Anal. Calcd. for 8.5 vinylidene fluoride copolymer: C, 31.59; H, 2.41; S, 3.83. Found: C, 31.79; H, 2.60; S, 3.93.

The analysis corresponds to a value of n of 8.5 and 36% by weight of comonomer IV. The water-washed polymer was a solid capable of being shaped or molded at elevated temperatures. In addition, a sample was dyed with Sevron® Red GL in the same manner as described above. A deep red-orange dyeing was obtained.

Utility Example A

All the novel acids of this application are very active cationic initiators, e.g., for tetrahydrofuran (THF) polymerization. A bulk polymerization was run at ca. 25° on 10 g of purified THF with 0.31 g of 2-ketopentafluoropropanesulfonic acid as initiator. Viscosity increased markedly in 30 min, but the polymerization was allowed to proceed for one day. Work-up was by quenching with 50 ml of concentrated ammonium hydroxide in 50 ml of distilled water followed by drying at 50° under full pump vacuum. A yield of 7.54 g of colorless, solid polytetrahydrofuran was obtained: $\eta_{inh}$ (0.1% in (CF$_3$)$_2$CHOH at 25°)=0.80.

Polytetrahydrofuran is a hydrolytically stable soft segment with good low temperature properties for incorporation into polyurethanes useful as elastomers and as spandex fibers. For example, F. Rodriquez, "Principles of Polymer Systems", McGraw-Hill, New York, N.Y., 1970, p. 424 cites homopolymers of tetrahydrofuran in the mol. wt. range 1000–3000 as useful components with diisocyanates.

I Claim:

1. A ketopolyfluorosulfonic acid of the formula

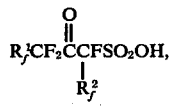

where $R_f^1$ and $R_f^2$, alike or different, are F or perfluoroalkyl of up to 4 carbons.

2. An acid of claim 1, 2-ketopentafluoropropanesulfonic acid.

* * * * *